US00PP22278P2

(12) United States Plant Patent
Zaiger et al.

(10) Patent No.: US PP22,278 P2
(45) Date of Patent: Nov. 29, 2011

(54) NECTARINE TREE NAMED 'SPRING FIRE'

(50) Latin Name: ***Prunus persica* var. *nucipersica***
Varietal Denomination: Spring Fire

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 12/803,146

(22) Filed: Jun. 21, 2010

(51) Int. Cl.
*A01H 5/00* (2006.01)

(52) U.S. Cl. ..... Plt./190

(58) Field of Classification Search ..... Plt./190
See application file for complete search history.

*Primary Examiner* — Susan McCormick Ewoldt

(57) ABSTRACT

A new and distinct variety of nectarine tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Having a low winter chilling requirement of approximately 300 hours at or below 45° F.
3. Fruit ripening in the early maturity season.
4. Fruit with a high degree of attractive red skin color.
5. Heavy and regular production of large size fruit.
6. Firm, yellow flesh with very good flavor and eating quality.

1 Drawing Sheet

Botanical classification: *Prunus persica* var. *nucipersica.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine and peach trees, which are known to us, and mentioned herein, 'Royal Glo' Nectarine (U.S. Plant Pat. No. 8,281), 'Fayette' Peach (non-patented), 'Royal April' Peach (U.S. Plant Pat. No. 3,411), 'Ruby Gold' Nectarine (U.S. Plant Pat. No. 3,101), 'May Glo' Nectarine (U.S. Plant Pat. No. 5,245), 'Honey Kist' Nectarine (U.S. Plant Pat. No. 9,333), 'Bonita' Peach (non-patented), 'May Grand' Nectarine (U.S. Plant Pat. No. 2,794), 'May Crest' Peach (U.S. Plant Pat. No. 4,064), 'Desert Gold' Peach (non-patented) and the proprietary seedlings '3W11', '202LK334' and '58ZA724'.

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was developed by us in our experimental orchard located near Modesto, Calif. as a first generation cross between two proprietary seedlings with the field identification numbers of '202LK334' and '58ZA724'. The seed parent (202LK334) originated from crosses between the following varieties; 'Royal Glo' Nectarine (U.S. Plant Pat. No. 8,281), 'Fayette' Peach (non-patented), 'Royal April' Peach (U.S. Plant Pat. No. 3,411), 'Ruby Gold' Nectarine (U.S. Plant Pat. No. 3,101) and 'May Glo' Nectarine (U.S. Plant Pat. No. 5,245). The pollen parent (58ZA724) originated from crosses between the following varieties; 'Honey Kist' Nectarine (U.S. Plant Pat. No. 9,333), 'Bonita' Peach (non-patented), 'May Grand' Nectarine (U.S. Plant Pat. No. 2,794), 'May Glo' Nectarine (U.S. Plant Pat. No. 5,245), 'May Crest' Peach (U.S. Plant Pat. No. 4,064), 'Desert Gold' Peach (non-patented) and a proprietary peach seedling with the identification number '3W11' (unknown parentage). A large group of these first generation seedlings were grown on their own root system and budded to older trees of 'Nemaguard' Rootstock (non-patented), to accelerate rapid fruit production for evaluation. Under close and careful observation we recognized the desirable fruit characteristics of the present new variety and selected it in 2002 for further asexual propagation and commercialization.

ASEXUAL REPRODUCTION OF THE VARIETY

Asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of nectarine tree is of large size, vigorous, upright growth, a productive and regular bearer of large size, firm, yellow flesh, clingstone fruit. The tree has a low winter chilling requirement of approximately 300 hours at or below 45° F. The fruit is further characterized with good flavor and eating quality, having a high degree of attractive red skin color and ripening in the early maturity season. In comparison to its seed parent (202LK334), the fruit of the new variety is larger in size and ripens approximately 27 days earlier. In comparison to its pollen parent (58ZA724), the fruit of the new variety has firmer flesh, more attractive red skin color, is larger in size, and ripens in the same early maturity season.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 7 year old specimens grown near Modesto, Calif., with color in accordance with Munsell Book of Color.

Tree:

*Size.*—Large, usually pruned to 3 to 3.5 meters in height and 3 meters in width for economical harvesting of fruit. Size varies with different cultural practices.

*Vigor.*—Vigorous, growth of 1.5 to 2.5 meters the first growing season. Varies slightly with type and fertility of soil, climatic conditions and cultural practices.

*Form.*—Upright, usually pruned to vase shape.

*Branching habit.*—Upright, crotch angle approximately 35°, increases with heavy crop load.

*Productivity.*—Productive, normal fruit thinning necessary for desirable market size fruit. Fruit set varies with climatic conditions during bloom season.

*Bearer.*—Regular, adequate fruit set 5 consecutive years.

*Fertility.*—Self-fertile.

*Density.*—Medium dense, pruning to open center of tree to vase shape desirable to enhance fruit color and keep fruit wood healthy.

*Hardiness.*—Hardy in all stone fruit growing areas of California. Tree grown in USDA Hardiness Zone 9. Winter chilling requirement approximately 300 hours at or below 45° F.

Trunk:

*Size.*—Large, circumference of 52.1 cm at 30.5 cm above the ground on a 7 year old tree.

*Stocky.*—Medium stocky.

*Texture.*—Medium shaggy, roughness increases with age.

*Color.*—Varies from 10YR 4/2 to 10YR 3/2.

Branches:

*Size.*—Medium. Average circumference 14.9 cm at 1.2 meters above ground. Crotch angle approximately 35°, increases with crop load.

*Surface texture.*—New growth relatively smooth. Mature growth medium rough, roughness increases with age.

*Lenticels.*—Average 18 in a 25.8 sq cm section. Average length 4.0 mm. Average width 1.6 mm. Color varies from 10YR 6/6 to 10YR 6/8.

*Color.*—New growth varies from 2.5GY 6/8 to 5GY 6/6 with 5R 4/8 where exposed to the sun. Old growth varies from 10YR 3/2 to 2.5Y 4/2, varies with age of growth.

Leaves:

*Size.*—Medium to large. Average length 126.9 mm. Average width 42.7 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slightly indented over midrib and leaf veins. Lower surface relatively smooth except for ridges caused by midrib and pinnate venation. Both surfaces glabrous.

*Petiole.*—Average length 8.6 mm. Average width 1.6 mm. Surface glabrous. Longitudinally grooved. Color varies from 5GY 6/8 to 5GY 5/6.

*Glands.*—Reniform. Size — medium to large. Average length 1.5 mm. Average diameter 1.1 mm. Number varies from 1 to 4, average number 3. Located primarily on the base of the leaf blade and the upper portion of the petiole. Color varies from 2.5GY 6/6 to 5GY 7/8.

*Stipules.*—Average number 2. Average length 11.7 mm. Edges — doubly serrate. Color varies from 2.5GY 7/6 to 5GY 7/6.

*Color.*—Upper surface varies from 5GY 4/8 to 5GY 3/6. Lower surface varies from 2.5GY 4/4 to 5GY 5/4. Midvein color varies from 2.5GY 7/6 to 5GY 7/6.

Flower buds:

*Size.*—Medium to large. Average length 15.2 mm. Average diameter 10.3 mm.

*Hardiness.*—Hardy with respect to California winters.

*Form.*—Plump, conical, becoming elongated before opening.

*Pedicel.*—Average length 3.7 mm. Average width 1.0 mm. Color varies from 2.5GY 6/6 to 5GY 6/6.

*Color.*—Varies from 7.5RP 8/4 to 7.5RP 7/8.

Flowers:

*Date of first bloom.*—Feb. 10, 2010.

*Date of petal fall.*—Feb. 18, 2010, varies slightly with climatic conditions.

*Size.*—Large, showy. Average height 18.5 mm. Average diameter 30.8 mm.

*Petals.*—Normally 5, alternately arranged to the sepals. Form — nearly globose, base narrows at point of attachment. Margin — sinuate. Average length 17.0 mm. Average width 14.8 mm. Color varies from 5RP 8/6 to 7.5RP 8/4, fades with age of flower.

*Sepals.*—Normally 5, alternately arranged to petals. Shape — triangular, apex rounded. Margin — entire. Average length 6.7 mm. Average width 5.9 mm. Upper surface glabrous, lower surface pubescent. Color — upper surface varies from 2.5GY 4/6 to 5R 3/4. Lower surface varies from 5R 3/4 to 5R 3/6.

*Stamens.*—Average number per flower 45. Average filament length 14.1 mm. Filament color N 9.5/ (white). Anther color varies from 10R 4/10 to 10R 3/8.

*Pollen.*—Self-fertile. Color varies from 5Y 8/10 to 5Y 7/10.

*Pistil.*—Normally 1. Surface — glabrous. Average length 18.3 mm. Position of stigma — average of 1.0 mm above anthers. Color varies from 10Y 8/6 to 2.5GY 8/6.

*Fragrance.*—Very slight.

*Color.*—Varies from 5RP 8/6 to 7.5RP 8/4.

*Number flowers per flower bud.*—One.

*Pedicel.*—Average length 4.7 mm. Average width 1.4 mm. Color varies from 2.5GY 6/6 to 5GY 7/6.

Fruit:

*Maturity when described.*—Firm ripe.

*Date of first picking.*—May 8, 2010.

*Date of last picking.*—May 15, 2010, varies slightly with climatic conditions.

*Size.*—Large. Average diameter axially 55.2 mm. Average transversely in suture plane 64.8 mm. Average weight 144.8 grams, varies slightly with fertility of the soil, amount of thinning and climatic conditions.

*Form.*—Globose.

*Suture.*—Nearly smooth to very slightly lipped. Extends from base to apex.

*Ventral surface.*—Very slightly lipped.

*Apex.*—Slightly retuse.

*Base.*—Retuse.

*Stem cavity.*—Rounded to slightly elongated in suture plane. Average depth 3.7 mm. Average diameter 6.2 mm.

Stem:

*Size.*—Small. Average length 8.9 mm. Average diameter 2.9 mm.

*Color.*—Varies from 2.5GY 6/8 to 5GY 6/8.

Flesh:

*Ripens.*—Relatively even, slightly earlier at the apex.

*Texture.*—Firm, meaty.

*Fibers.*—Few, small, tender.

*Firmness.*—Good, holds firm on the tree 6 to 7 days after maturity.

*Aroma.*—Moderate.

*Amydgalin.*—Undetected.

*Eating quality.*—Good.

*Flavor.*—Good, good balance between acid and sugar.

*Juice.*—Moderate amount, enhances flavor.

*Brix.*—Average Brix 10.0°, varies slightly with amount of fruit per tree and climatic conditions.

*Pit cavity.*—Average length 36.3 mm. Average width 25.6 mm. Average depth 11.0 mm. Color varies from 5Y 8/8 to 5Y 7/8.

*Color.*—Varies from 2.5Y 8/12 to 5Y 8/8.

Skin:

*Thickness.*—Medium.

*Surface.*—Smooth.

*Pubescence.*—Wanting.

*Tendency to crack.*—None.

*Color.*—Ground color varies from 5Y 8/8 to 5Y 7/8. Overspread with 7.5R 3/12 to 5R 2/4.

*Tenacity.*—Tenacious to flesh.

*Astringency.*—None.

Stone:

*Type.*—Clingstone.

*Size.*—Large. Average length 36.3 mm. Average width 25.6 mm. Average thickness 21.8 mm.

*Form.*—Ovate.

*Base.*—Varies from flat to rounded.

*Apex.*—Varies from round to slightly pointed. Average length 0.5 mm.

*Surface.*—Pitted throughout, pits vary from rounded to slightly elongated.

*Sides.*—Unequal, with one side extending further from suture plane.

*Ridges.*—Numerous small ridges extending from base to apex, relatively smooth.

*Tendency to split.*—Slight.

*Color.*—Varies from 2.5Y 8/6 to 10YR 5/8 when dry.

Kernel:

*Size.*—Medium. Average length 17.5 mm. Average width 14.1 mm. Average depth 6.0 mm.

*Form.*—Ovate.

*Viability.*—Poor, embryo only partially developed.

*Skin.*—Varies from 2.5Y 9/4 to 2.5Y 8.5/4.

Use: Dessert.

*Market.*—Local and long distance.

Keeping quality: Good, held firm in cold storage at 38° to 42° F. for 2 weeks without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, substantially as illustrated and described.

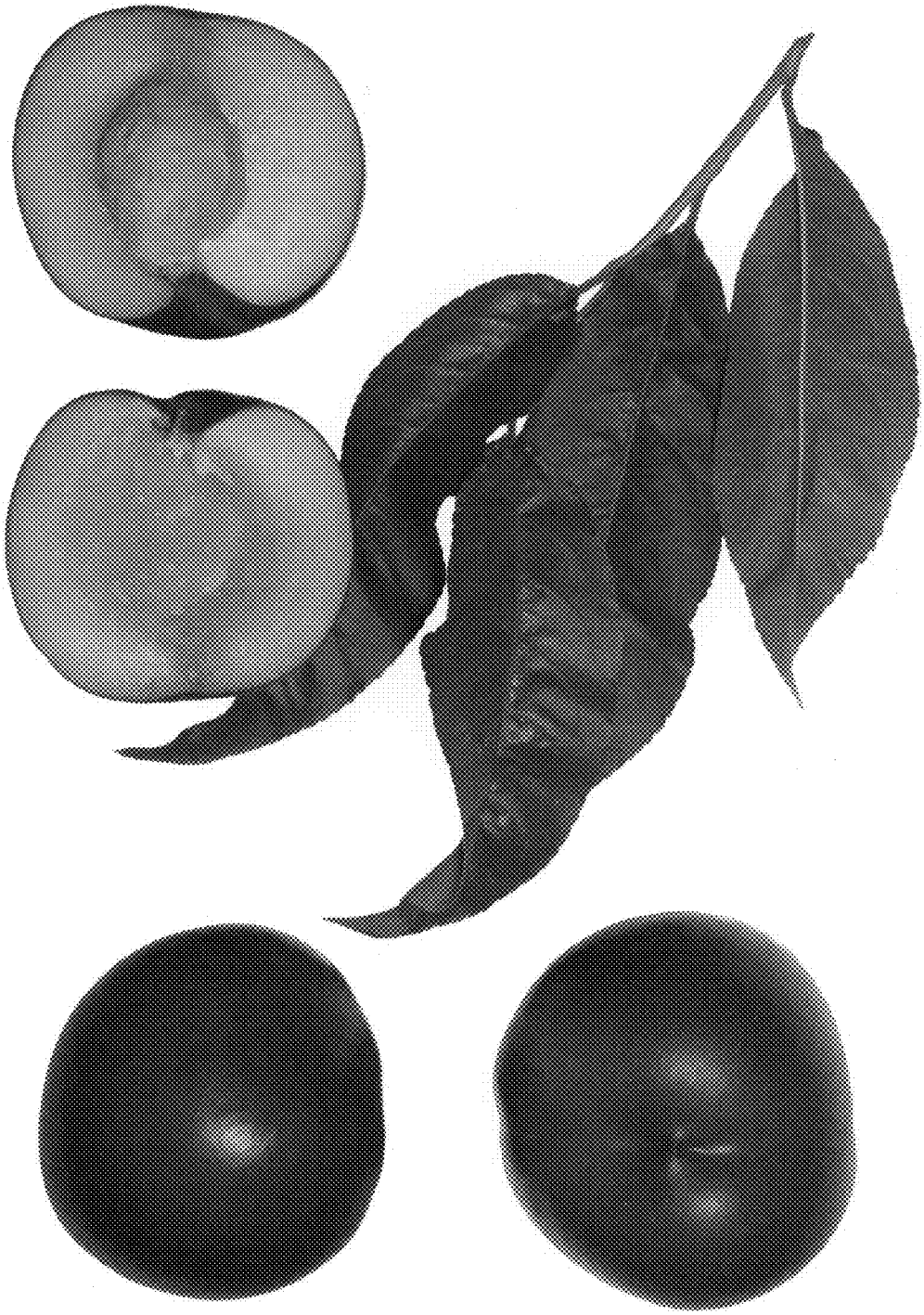

* * * * *